(12) United States Patent
Hasling (10) Patent No.: US 9,277,964 B1
(45) Date of Patent: Mar. 8, 2016

(54) LASER TREATMENT OF BODY INJURIES AND DEFECTS

(75) Inventor: Thomas Alan Hasling, Honolulu, HI (US)

(73) Assignee: OCEANIT LABORATORIES, INC., Honolulu, HI (US)

( * ) Notice: Subject to any disclaimer, the term of this patent is extended or adjusted under 35 U.S.C. 154(b) by 647 days.

(21) Appl. No.: 12/976,199

(22) Filed: Dec. 22, 2010

Related U.S. Application Data (60) Provisional application No. 61/284,620, filed on Dec. 22, 2009.

(51) Int. Cl.
*A61B 5/05* (2006.01)
*A61B 18/20* (2006.01)
*A61B 5/055* (2006.01)

(52) U.S. Cl.
CPC .............. *A61B 18/203* (2013.01); *A61B 5/055* (2013.01)

(58) Field of Classification Search
CPC ............. A61B 19/5244; A61B 18/203; A61B 2018/00452
USPC .......... 600/310, 407, 473, 475–477; 606/2, 3, 606/13
See application file for complete search history.

(56) References Cited

U.S. PATENT DOCUMENTS

| | | | |
|---|---|---|---|
| 6,594,513 B1 * | 7/2003 | Jobsis et al. | 600/328 |
| 8,060,189 B2 * | 11/2011 | Ben Dor et al. | 600/476 |
| 2003/0109906 A1 * | 6/2003 | Streeter | 607/88 |

OTHER PUBLICATIONS

Dual-phase lag effects on thermal damage to biological tissues caused by laser irradiation, Zhou et al., Computers in Biology and Medicine 39 (2009) 286-293.
Bio-heat transfer analysis during short pulse laser irradiation of tissues, Jaunich et al., International Journal of Heat and Mass Transfer 51 (2008) 5511-5521.
Minimally invasive techniques in the treatment of saphenous varicose veins, Nijsten et al., J Am Acad Dermatol vol. 60, No. 1, 110-119.
Endovenous therapies of lower extremity varicosities: A meta-analysis, van den Bos et al., Journal of Vascular Surgery vol. 49, No. 1, 230-239.
Systematic Review of Treatments for Varicose Veins, Leopardi et al., Ann Vasc Surg. Mar. 2009;23(2):264-76.

(Continued)

*Primary Examiner* — James Kish
(74) *Attorney, Agent, or Firm* — Symbus Law Group, LLC; Clifford D. Hyra (57) ABSTRACT

Wave energy is directed into a body. A condition within the body is observed by reflection from effects within the body. An internal target is located. Wave energy is focused on the target within the body and is increased in intensity to treat the target. A hand held instrument passivates or moves scalp from a skull, and converges, diverges or collimates near infrared laser beams through a skull and into interior tissue. Reflected energy reveals vessels edema or bleeding. Vessel targets are identified. Infrared laser beams are directed, triggered and intensified to coagulate or constrict the vessel. The hand held instrument is a wand connected to a laser source, processor, display and power source. The power supply, processor, infrared laser, display and laser director are mounted on a hand held unit for field use by technicians and medics to prevent time delay and further injury.

30 Claims, 3 Drawing Sheets

(56) References Cited

OTHER PUBLICATIONS

Systematic Review of Endovenous Laser Therapy Versus Surgery for the Treatment of Saphenous Varicose Veins, Hoggan et al., Ann Vasc Surg. Mar. 2009;23(2):277-87.

An axisymmetric dual-phase-lag bioheat model for laser heating of living tissues, Zhou et al., International Journal of Thermal Sciences 48 (2009) 1477-1485.

* cited by examiner

LASER TREATMENT OF BODY INJURIES AND DEFECTS

This application claims the benefit of U.S. Provisional Application No. 61/284,620, filed Dec. 22, 2009, which is hereby incorporated by reference in its entirety as if fully set forth herein.

This invention was made with Government support under Contract W911NF-09-C-0075 awarded by U.S. Army Research Office/DARPA. The Government has certain rights in this invention.

BACKGROUND OF THE INVENTION

Intracranial bleeding following head trauma is a major medical concern for the modern U.S. warfighter and civilian population. Since there is no practical point of injury treatment for intracranial bleeding, death or permanent neurological injury becomes increasingly likely as treatment is delayed during transportation to a medical treatment facility.

Battlefield and point of injury treatment of intracranial hemorrhage is nearly nonexistent. There is very little a field medic or first responder can do to mitigate the consequences of intracranial bleeding in the first moments after injury. The best option available to the medical personnel is to prepare the patient for rapid evacuation to a surgically capable medical treatment facility. The unfortunate consequence is that neurological damage or death becomes increasingly likely as time passes. This applies to civilian situations as well. Closed head injuries are very common injuries resulting from automobile accidents, blunt trauma, and sports injuries. Cranial hypothermia has been used for many years in an attempt to slow the progression of central damage. Hypothermia is intended to reduce inflammation, limit bleeding, and retard metabolism. This technique has been demonstrated to reduce the long-term neurological injury resulting from aneurysm; however, this technique is logistically impractical on the battlefield or accident site and does little to address the underlying cause.

Closed head injuries with edema greater than 1 cm$^2$ have a mortality rate of 89%. The time from injury to treatment is of critical importance in the treatment of intracranial hemorrhage. Classically, superficial intracranial hemorrhage is treated by drilling a burr hole through the skull to relieve intracranial pressure. If the patient survives, a neurovascular surgeon would then intervene to stop the bleeding. Unfortunately, the classical medical and surgical intervention is limited to the medical treatment facility, long after the progression of the injury may have become fatal.

Traumatic brain injury (TBI) resulting from intracranial hemorrhage is a major cause of death and permanent disability for modem warfighters and in the civilian sector. Advances in protective body armor have contributed to the reduction in U.S. warfighter mortality. Injured warfighters that would have previously suffered fatal bodily wounds are presenting with injuries such as TBI. The TBI damage resulting from the initial blast or concussion is commonly exacerbated by subsequent intracranial bleeding. Intracranial hemorrhage commonly occurs when the soft tissues are displaced relative to the skull and meninges, creating damaging shearing and crushing forces. As the hemorrhage progresses, the blood confined in the volume of the skull displaces the brain, further damaging the tissues. Additionally, the intracranial pressure increases with the blood pressure from an arterial rupture. This increased pressure resists adequate blood flow to all the tissues within the closed volume resulting in widespread neurological damage. The options for point-of-injury treatment are severely limited. If the injured patient survives the transport to a treatment facility, a burr hole and craniotomy are the first line of treatment. Significant time may pass between injury and treatment, usually resulting in additional disability or death. Field medics and medical-evacuation personnel are substantially unequipped to treat intracranial bleeding in the first critical moments following injury. Point-of-injury treatment of intracranial bleeding would decrease the extent of secondary insults and decrease mortality.

SUMMARY OF THE INVENTION

This invention provides detection and treatment of injuries and defects and laser detection and laser actuated hemostasis and treatment in deep tissues.

The invention provides:
intracranial hemostasis (primary)
hemostasis in other parts of the body
treatment of hemorrhagic stroke or other cerebrovascular accident
non-invasive surgery (e.g., tubal ligation, non-invasive polyp removal, targeting leaky arteries around tumors, removal of tumors, kidney stones, meningeal cysts);
detection and destruction of target probes specific to cell type or tissue (e.g. probe armed antibodies)
destruction of specific organisms or molecules (e.g., malaria, parasites, crystals of urea)
treatment of vascular spasm (e.g., headaches)
targeted therapy in other tissues The new invention reduces the need for immediate invasive surgical procedures and reduces morbidity and mortality.

The invention may be image-guided, e.g., by ultrasound or fluoroscope imaging of the target under the guidance of a surgeon. The invention uses laser energy to treat superficial intracranial hemorrhage. This new technology is minimally invasive and is intended to be used at the point of injury, during transport, and/or at medical treatment facilities. The imaging/diagnostic system can provide targeting information for automatic treatment or manual treatment. The targeting can also be achieved via anatomical landmarks. Initial treatment is available in minutes rather than hours.

The invention is intended to be minimally invasive and can be used, among other things, to treat superficial intracranial hemorrhage. The invention detects and locates an arterial hemorrhage then non-invasively delivers controlled energy pulses to produce hemostasis, while preserving the deeper and surrounding tissues. Hemostasis is achieved by either photocoagulating the ruptured artery or inducing vasoconstriction (i.e. vasospasm) of the proximal or feeding vessel. For example, the middle meningeal artery is ruptured in many TBI cases; the hemostatic treatment may be targeted to the hemorrhage site on a branch of the meningeal artery or to the main feeding vessel.

Skulls and soft tissues are not highly absorbing to near infrared light wavelengths (800-1200 nm). Various tissues preferentially absorb and transmit different regions of the spectrum. Taking advantage of the spectral characteristics of the tissues, the invention specifically targets the damaged vessel and the blood, with limited impact on neural tissues. LIDAR technologies are capable of measuring Doppler shifts of turbulent flows, such as blood pulsing from a ruptured artery. Doppler shift reflected detection functions in a manner similar to the way ultrasound is used to detect aberrant blood flow such as cardiac valve leakage. Alternatively, ultrasound techniques or other imaging modalities may be used to detect a ruptured artery. Normal, laminar, non-turbulent blood flow is differentiated from hemorrhaging flow. Superficial intracranial arterial bleeding produces turbulent pockets in the soft tissues.

Upon detecting a target, for example a hemorrhage, the invention delivers a laser pulse that preferentially photocoagulates the site. Alternatively, the hemostasis pulse is targeted at the proximal arterial wall adjacent to the rupture or upstream to the rupture. Targeting the arterial wall with the high energy pulses will alternatively induce vasoconstriction rather than complete coagulation, thereby preserving the artery for subsequent vascular surgery. The central wavelength of the hemostatic laser is tuned to the preferential absorbance of the arterial wall or to oxygenated blood, for example 976 or 1064 nm. Thus, the laser energy preferentially targets the appropriate tissues and minimizes collateral damage to surrounding tissues such as the dura mater and brain. The hemostatic laser may include the following characteristics or setup:

- Continuous wave or pulsed laser can be used to arrest or minimize the blood flow.
- For pulsed lasers, waveform shaping (e.g., amplitude modulation, ramping) will be applied for maximum energy deposition or vasoconstriction.
- The laser power density ranges is from 0.01 $W/cm^2$ and higher.
- The laser can be directed through an optical fiber, in free space, or other light guide.
- A combination of laser wavelengths or in a crossed beam/multibeam setup can be used to further enhance energy deposition to selected targets.
- Adaptive optics may be used to increase energy deposition at the target and compensate for wave front distortion and scattering.
- The laser with a free fiber end may be used to deliver this energy.
- The beam can be convergent, collimated, or divergent.
  - The pulse beam can be highly convergent so that the focal point of the laser is confined to a specific volume such that superficial and deeper tissues are preserved, much like laser eye surgery.
  - The pulse beam can be collimated or divergent to ensure that the area of interest is well within the beam path but never culminates into a focal point.

Methods may be employed to preserve the superficial layers. This is important because it the skin or other tissues are blackened they become a photon sink and this prevents subsequent photons from penetrating to the deeper tissues. A variety of methods might be employed to preserve the superficial tissues including:

- active cooling the surface (e.g., Peltier technology);
- passive cooling using liquids or gels;
- improved optical coupling to the surface using refractive index match substances such as gels or oils;
- use of heat sinks;
- direct contact with the surface using a transparent material that will also act as a heat sink and improve optical coupling; and
- chemical or photo modification of the superficial layers to make them more transparent.

Hair removal or an excision technique to remove the superficial tissues (e.g., skin punch biopsy) may be employed to further increase transparency. Hair removal may be executed by physical, photo, or chemical means. The biopsy technique includes the following components:

- use of a canula or hypodermic needle to remove or bypass the superficial tissue.
- application of a burr or laser fiber to remove or ablate, respectively, residual tissue on the skull.
- introduction of a nucleation site to increase site specific energy deposition of the laser.

This technology gives the patient and providers additional time for medical and surgical intervention. The new invention will be implemented at several points of care: on the battlefield (point of injury), in transit, and throughout the echelons of medical care (e.g., sports medicine, emergency and operating rooms). The device is intended to be small (canteen sized) and may incorporate a fiber-optic-coupled wand. The invention may be powered by portable power supply (e.g. batteries), from a mobile source (e.g. vehicle), or fixed source (e.g. building power).

The invention determines and delivers adequate and specific pulse energy through tissues. Vasoconstriction require different amounts of energy for delivering and modulating the energy pulses to appropriately modify the target.

Temperature gradients surrounding targeted volume are important. Isolating the hemostasis pulse energy to as small of a volume as possible reduces the impact on healthy tissues.

A significant requirement is to preserve the surrounding tissues while effectively targeting the appropriate tissues. Undesired heating of the surrounding tissues is limited by selecting the appropriate laser wavelengths, focusing the energy into a small volume, distributing background light, or cooling tissues.

The invention detects, targets, and mitigates hemorrhages. Upon targeting a hemorrhage, the hemostatic pulse coagulates or vasoconstricts the ruptured artery in varying anatomical locations and laser conditions.

Non-invasive detection and treatment of intracranial hemorrhage is an important object of this invention. Intracranial hemorrhage is a significant problem for the modem warfighter. The pattern of injuries in accidents and conflicts indicates a dire need for improved point-of-injury treatment. There are currently no effective intracranial hemostasis treatments available to field medical personnel. Delivering adequate and specific hemostatic energy, while preserving the surrounding tissues is important.

The invention provides a laser Doppler shift detection system considering depth, flow rate, and vessel diameter and delivers adequate and specific hemostatic pulse energy, and determines temperature gradients surrounding targeted volume. The invention may also include other imaging techniques such as ultrasound, transcranial Doppler, or other optical or radiological techniques.

The new invention provides an excellent system for field medics and first responders to treat many cases of internal bleeding. For example, the new invention is suitable for the treatment of intracranial hemorrhage. Additionally, the new invention discriminates between the tissues that are involved. Laser energy is tuned to preferentially target blood and arterial walls and avoid neural tissues.

Laser medical therapy is well established for vascular treatments. In particular, varicose vein laser therapy is common and considered safe. Varicose vein laser treatment uses laser energy to constrict and reduce varicose veins, even the large saphenous veins. Those systems are typically designed for manual targeting of the vessel. The target vein is visible to the provider and very superficial, which accommodates the manual nature of the targeting and therapy.

The present invention uses near infrared laser energy (or other imaging modalities) to detect and locate intracranial hemorrhage and to locate damaged arteries and specifically delivers laser energy at the proximal artery to constrict or coagulate the artery until further medical treatment is available.

These and other objects and features of the invention are apparent in the disclosure, which includes the above and ongoing written specification, with the claims and the drawings.

DETAILED DESCRIPTION OF THE DRAWINGS

As shown in FIGS. 1-8, the invention maybe comprised of several components. The laser source 1 (diode or other variety of laser) generates the laser energy. The power is supplied to the laser source via a power source 8. Depending on the duration and desired fidelity of the laser coherence, a cooling system 2 may be used to cool the laser source. The cooling system may be active (e.g. Peltier, refrigerant, or pumped fluids) or passive in the form of a heat sink. The laser source may be coupled by a light guide 3 (e.g. fiber optic or liquid guide) to the handheld wand 5. The handheld wand might also be optically coupled directly to the laser source via an optical lens system and the whole invention maybe handheld. The handheld wand may incorporate an imaging transducer (e.g. transcranial doppler, optical imaging, or radiological imaging) that provides imaging feedback to the imaging system 9. The image signal is relayed to the imaging system via an image cable 11. The invention maybe controlled manually or automatically. The imaging system can provide feedback for the user to decide to manually trigger the laser pulse. Alternatively, the imaging system may have an algorithm to analyze the imaging data and automatically trigger the laser pulse. The system settings such as detection thresholds, pulse intensity, pulse duration, pulse repetition, and others setting will be controlled via a user interface 10. The manual trigger 4 might be located on the handheld wand or user interface control panel. When the laser source is activated and laser energy is passed to the wand via the light guide to optical elements in the handheld wand 5 that will either cause the laser beam 7 to converge, diverge, or collimate. The tissues of the treated patient 12 will have a tendency to scatter the laser beam. An adaptive optics system 6 might be incorporated into the invention to accommodate for the tissue induce scatter and maintain the intended beam profile.

The laser energy will be delivered into the patient through the intervening tissues—e.g. scalp/skull 12 and the dura mater 13. When targeting intracranial targets, the deeper tissues might include the arachnoid mater 14 and the brain tissues 15. The intended target of the invention may be the meningeal arteries 16 supplying the dura mater, deeper cerebral vessel 23, or other targets. The optical tip 17 of the handheld wand is place to the patient's head or body surface. In order improve energy delivery to the intended target several configurations might be used. Three of these configurations are represented in FIGS. 2, 3 and 4, Panels A, B, and C.

Figure 1:
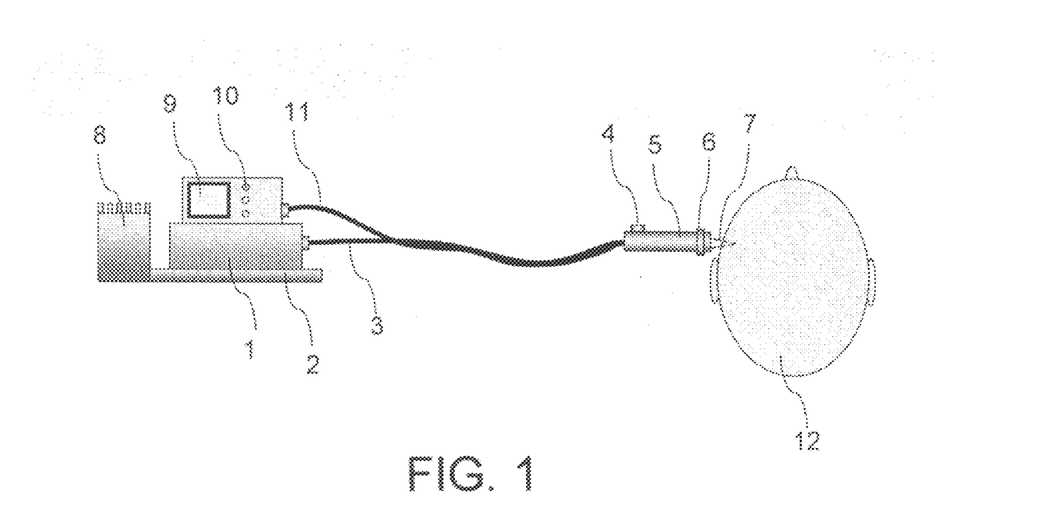
FIG. 1 is a schematic representation of one embodiment of the laser system of the invention.
Figure 2:
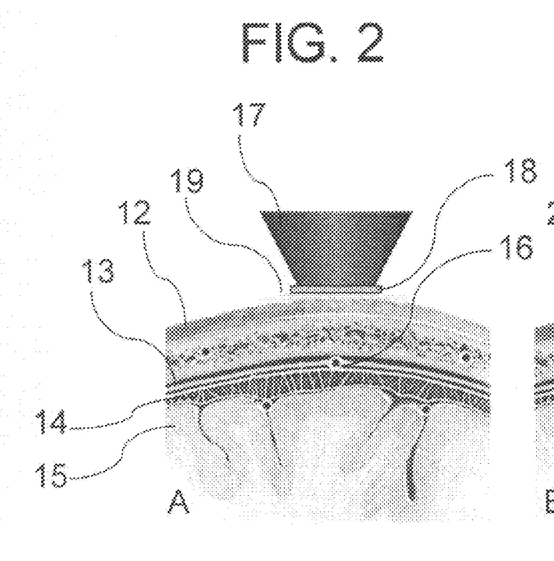
FIG. 2 is a schematic representation of a laser tip with a laser window and gel contacting a skin and skull.

FIG. 2, Panel A represents a technique where the laser energy is passed through the scalp and skull. An optical window 18 and/or optical coupling gel/fluid 19 may be used. The window and gel improves penetration of the laser energy through the intervening tissues and protects the surface from being burned/carbonized. The window and gel can act as a passive heat sink or be actively cooled.

Figure 3:
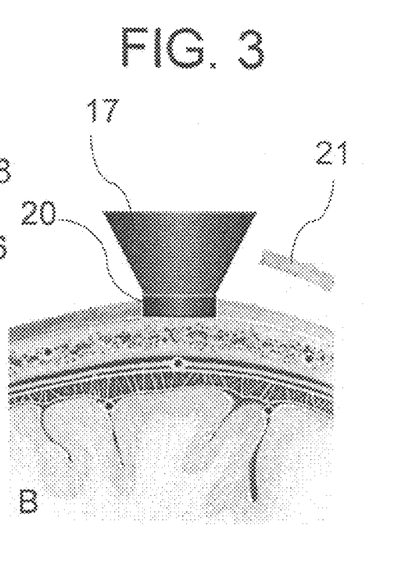
FIG. 3 is a schematic representation of a laser tip with a punch cannula for removing a plug of skin and preventing flow of fluids toward the removal site.

FIG. 3, Panel B represents a technique where the superficial tissues 21 are punched/excised so the laser energy does not need to pass through them. The tip of the wand might include the cannula cutting device 20 that cuts through the tissues. The cannula will also act as a barrier to prevent blood and other fluids from flowing into the created volume. The laser energy can then pass through the bone or a configuration similar to FIG. 2, Panel A can be place directly against the skull surface.

Figure 4:
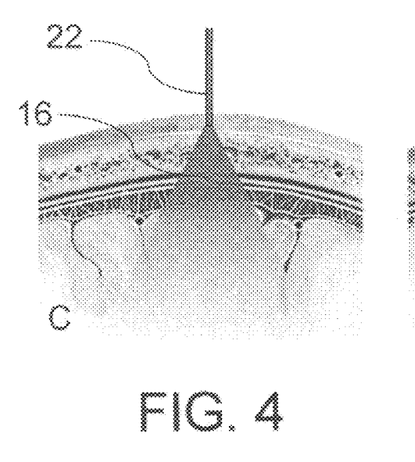
FIG. 4 is a schematic representation of a canula or needle laser guidance tip to bypass the scalp.
Figure 5:
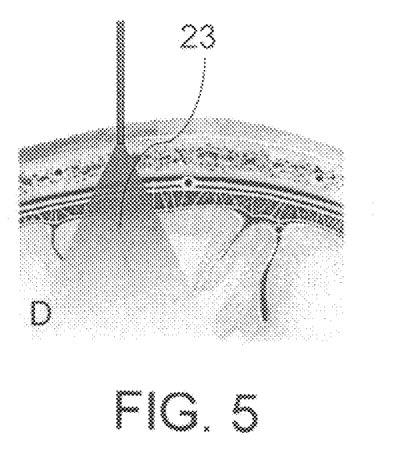
FIG. 5 is a schematic representation of delivering laser energy to a deeper vessel.

FIG. 4. Panel C represents a technique similar to FIG. 3. Panel B; however rather than excising tissue, a sharp canula 22 or hypodermic needle-like device is passed through the superficial tissues (displacing the tissues laterally) to gain access to the skull surface or deeper structures. The laser energy is then passed through the canula to the intended target. The target might be the superficial meningeal vessels 16, deeper vessels 23, or other targets.

Figure 6:
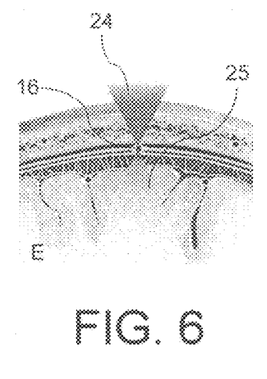
FIG. 6 is a schematic representation of a focused laser beam.
Figure 7:
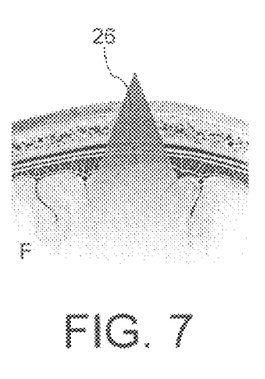
FIG. 7 is a schematic representation of a divergent laser beam.
Figure 8:
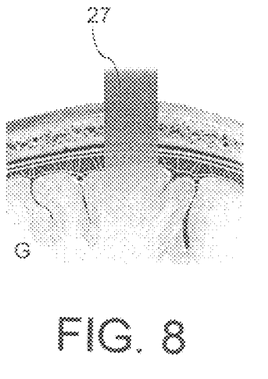
FIG. 8 is a schematic representation of a collimated laser beam.

The beam profile may be focused/converging 24 as shown in FIG. 6, Panel E, and specifically directing energy to the target 16. Once the beam fully converges it will then proceed to diverge 25. This divergence will distribute the total laser energy over a larger area, limiting the impact on the non-targeted tissues (e.g. brain 15). Alternatively, the laser beam can be divergent 26 or collimated 27, as shown in FIGS. 7 and 8, Panels F and G with the energy spread substantially evenly across the beam profile. These beam configurations are not focused but rather treat the area illuminated by the beam. Since, the beams are spread over a larger area than the focusing beam 24, the impact on background tissues will be minimized.

Another configuration of the beams might include multiple beams originating from different surface locations and the beams are directed and converge upon a single target. The beams in a multiple beam arrangement can be converging, diverging, or collimated. Using multiple beams will create high energy densities at the target but have lower energy densities on the intervening and deeper tissues.

Applications of the invention include, for example:
- intracranial hemostasis (most importantly epidural hematoma resulting from rupture of the middle meningeal artery).
- hemostasis in other parts of the body (e.g. femoral artery, other large arteries, or in organs),
- treatment of hemorrhagic stroke or other cerebrovascular accident (targeting cerebral arteries or veins),
- non-invasive surgery (e.g., tubal ligation, ectopic pregnancy removal, non-invasive polyp removal, targeting leaky arteries around tumors, removal of tumors, kidney stones, meningeal cysts),
- detection and destruction of target probes specific to cell type or tissue (e.g. probe armed antibodies), Functions of the invention include, for example: image-guided (ultrasound, MRI, xray, etc.),
- Ultrasound detection of blood flow,
- LIDAR detection of blood flow,
- manual targeting (anatomical landmarks),
- imaging/diagnostic system can provide targeting information for automatic treatment or manual treatment,
- hemostasis achieved by coagulation of the targeted artery,
- hemostasis achieved by inducing vasoconstriction of the proximal or feeding vessel.
- taking advantage of the spectral characteristics of the tissues, (The invention specifically targets the damaged vessel and the blood, with decreased impact on neural tissues and other surrounding tissues),
- the central wavelength of the hemostatic laser is tuned to the preferential absorbance of the arterial wall or to oxygenated blood, for example 976 nm or 1064 nm,
- other wavelengths also used,
- continuous wave or pulsed laser used to arrest or minimize the blood flow,
- for pulsed lasers, waveform shaping (e.g., amplitude modulation, ramping) applied for maximum energy deposition or vasoconstriction,
- the laser power density ranges from 0.01 $W/cm^2$ and higher,
- the laser can be directed through an optical fiber, in free space, or other light guide.
- a combination of laser wavelengths,
- in a crossed beam/multiband setup used to further enhance energy deposition to selected targets,
- adaptive optics used to increase energy deposition at the target and compensate for wave front distortion, scattering and undesired absorption,
- the laser with a free fiber end used to deliver the energy,
- the beam convergent, collimated, or divergent,
- methods employed to preserve the superficial layers, for example:
  - active cooling the surface (e.g., Pettier technology),
  - passive cooling using liquids or gels,
  - improved optical coupling to the surface using refractive index match substances such as gels or oils,
  - use of heat sinks,
  - direct contact with the surface using a transparent material that also acts as a heat sink and improve optical coupling,
  - chemical or photo modification of the superficial layers to make them more transparent,
  - hair removal or an excision technique to remove the superficial tissues, and
  - hair removal may be executed by physical, photo, or chemical means,
- use of a canula or hypodermic needle to remove or push aside the superficial tissue,
- application of a burr or laser to remove or ablate, respectively, residual tissue on the skull,
- introduction of a nucleation site to increase site specific energy deposition of the laser,
- implementation at several points of care: on the battlefield, point of injury, in transit, and throughout the echelons of medical care,
- powered by portable power supply (e.g. batteries), from a mobile source (e.g. vehicle), or fixed source (e.g. building power).
- minimally-invasive treatment of intracranial hemorrhage, laser energy tuned to preferentially target blood and arterial walls and to avoid neural tissues,
- to treat many cases of internal bleeding.
- laser source (diode or other variety of laser),
- a cooling system cools the laser source.

The cooling system is active (e.g. Peltier, refrigerant, or pumped fluids) or passive in the form of a heat sink The laser source is coupled by a light guide 3 (e.g. fiber optic or liquid guide) to the handheld wand 5

Handheld wand is optically coupled directly to the laser source via an optical lens system, and the whole system is handheld The handheld wand incorporate an imaging transducer (e.g. transcranial doppler or optical imaging) that provides imaging feedback to the imaging system 9.

The invention is controlled manually or automatically.

The imaging system provides feedback for the user to decide to manually trigger the laser pulse.

The imaging system includes an algorithm to analyze the imaging data and automatically trigger the laser pulse.

Settings such as detection thresholds, pulse intensity, pulse duration, pulse repetition, and others setting are controlled via a user interface When the laser source is activated, laser energy is passed to the wand via the light guide to optical elements in the handheld wand 5.

An adaptive optics system 6 is incorporated into the invention to accommodate for the tissue induce scatter and maintain the intended beam profile.

The laser energy is delivered into the patient through the intervening tissues—e.g. scalp/skull 12 and the dura mater 13.

The intended target of the invention is the meningeal arteries 16 supplying the dura mater, deeper cerebral vessels 23 or other targets.

The optical tip 17 of the handheld wand is place to the patient's head or body surface.

An optical window 18 and/or optical coupling gel/fluid 19 improves penetration of the laser energy through the intervening tissues and protects the surface from being burned and carbonized. The window and gel can act as a passive heat sink or are actively cooled.

Superficial tissues 21 are punched or excised.

A tip of the wand includes a cannula cutting device 20 that cuts through the tissues.

The cannula also acts as a barrier to prevent blood and other fluids from flowing into the created volume.

Rather than excising tissue, a sharp canula 22 or hypodermic needle-like device is passed through the superficial tissues (displacing the tissues laterally) to gain access to the skull surface or deeper structures.

The laser energy is then passed through the canula to the intended target through fiber, free space, lens system, fluid, or polymer.

beam profile may be focused/converging 24 and specifically directing energy to the target 16.

The laser beam can be divergent or the laser beam can be collimated.

Configuration of the beams include multiple beams originating from different surface locations, and the beams are directed to a single target. The beams in a multiple beam arrangement can be converging, diverging, or collimated.

I claim:

1. A system for internal therapeutic hemorrhage control and repair, comprising:

a power supply, a laser energy source connected to the power supply, an energy director connected to the laser source and arranged for delivering therapeutic laser energy through a human skull to target vessels around or within the brain of a human head in order to photocoagulate and/or vasoconstrict the target vessels to achieve hemostasis, a trigger connected to the energy director or to the laser source for activating delivery of the therapeutic laser energy, wherein the energy director comprises a cutting device configured to remove superficial tissue over the human skull and to act as a barrier after removal of the superficial tissue to prevent blood and other fluids from flowing into the created volume and interfering with delivery of the therapeutic laser energy.

2. The system of claim 1, wherein the energy director has an optical window, lens or other optical device, further comprising optical coupling gel or fluid interposed between the window and the target.

3. The system of claim 1, wherein the laser energy source is a near infrared laser source and the laser energy delivered to the target is focused, divergent or collimated.

4. The system of claim 1, further comprising a receiver connected to the energy director and a processor connected to a flow monitoring system.

5. The system of claim 1, wherein the power supply, one or more focusing lenses of the laser source, the energy director and the trigger are mounted together as an instrument configured to be held by hand.

6. The system of claim 1, further comprising plural laser beams simultaneously focused on a single point of the target for delivering laser energy to the target.

7. The system of claim 1, wherein the hand held energy director is configured to deliver the therapeutic laser energy in a divergent beam.

8. The system of claim 1, further comprising a Peltier device configured to cool the surface of the head where the laser energy touches.

9. The system of claim 1, wherein the therapeutic laser energy has a wavelength of between 976 and 1064 nm.

10. The system of claim 1, wherein the energy director is configured to deliver the therapeutic laser energy from inside the cutting device.

11. A method comprising providing internal therapeutic hemorrhage control and repair, further comprising:

providing a power supply, providing a laser energy source connected to the power supply, providing an energy director connected to the laser energy source and comprising a cutting device, delivering therapeutic laser energy through the human skull to target vessels around or within a brain within the skull in order to photocoagulate and/or vasoconstrict the target vessels to achieve hemostasis, removing superficial tissue over a human skull with the cutting device and blocking blood and other fluids from flowing into a volume created thereby and interfering with deliver of the therapeutic laser energy by holding the cutting device in place against the human skull, and providing a trigger connected to the energy director or to the laser source for activating delivery of the therapeutic laser energy.

12. The method of claim 11, wherein the therapeutic laser energy is delivered from inside the cutting device.

13. The method of claim 11, wherein the therapeutic laser energy has a wavelength of between 976 and 1064 nm.

14. A method for internal therapeutic hemorrhage control and repair, comprising:

locating an arterial hemorrhage within a skull of a patient;

pressing a laser light source against a patient's head to deliver the laser energy and removing superficial tissue layers where the laser light source is pressed against the patient's head to ease delivery of the laser energy through any remaining superficial tissue layers; and achieving hemostasis by at least one of:
  (a) photocoagulating a ruptured blood vessel by delivering near-infrared laser energy through the patient's skull and superficial tissue layers to the location of the arterial hemorrhage; and
  (b) delivering near-infrared laser energy through the patient's skull and superficial tissue layers to a blood vessel proximal to or feeding the ruptured blood vessel and inducing vasoconstriction of the proximal or feeding blood vessel.

15. The method of claim 14, wherein the delivered near-infrared laser energy preferentially targets blood and arterial walls and avoids neural tissues.

16. The method of claim 15, wherein the laser energy has a wavelength of between 976 and 1064 nm.

17. The method of claim 14, wherein removing superficial tissue layers comprises inserting a cannula through some of the superficial tissue layers, further comprising preventing blood and other fluids from flowing into a volume created by the cannula and interfering with the delivery of the laser energy by physically blocking the fluids with the cannula walls.

18. The method of claim 17, wherein removing superficial tissue layers comprises removing all superficial tissue between the surface of the patient's skin and the patient's skull so that the laser light source is pressed directly against the patient's skull.

19. The method of claim 17, wherein the laser energy is delivered from the inside of the cannula.

20. The method of claim 14, wherein the ruptured vessel is a branch of a middle meningeal artery and the laser energy is delivered to a main feeding blood vessel of the branch of the meningeal artery.

21. The method of claim 14, wherein the ruptured vessel is a deep cerebral vessel.

22. The method of claim 14, wherein the laser energy is delivered in pulses.

23. The method of claim 14, wherein the laser energy is delivered as a divergent beam.

24. The method of claim 14, further comprising cooling the surface of the patient's body where the laser light source is pressed against it to prevent carbonization of the superficial tissue layers.

25. The method of claim 14, further comprising determining temperature gradients surrounding an area where the laser energy is delivered to avoid damage to surrounding tissues.

26. The method of claim 14, further comprising directing the laser energy in the form of multiple beams originating from different surface locations on the patient's body and converging them on a single target location.

27. The method of claim 14, wherein hemostasis is achieved by photocoagulation.

28. The method of claim 14, wherein hemostasis is achieved by vasospasm.

29. The method of claim 14, wherein delivering near infrared laser energy through the patient's skull comprises pressing an energy director against the patient's head near the location of the arterial hemorrhage and activating a trigger.

30. The method of claim 29, further comprising holding the energy director and a connected power supply and laser energy source by hand and manually pressing the energy director to the patient's head.

\* \* \* \* \*